(12) United States Patent
Iyer et al.

(10) Patent No.: US 8,160,707 B2
(45) Date of Patent: Apr. 17, 2012

(54) METHOD AND APPARATUS FOR MINIMIZING EMI COUPLING IN A FEEDTHROUGH ARRAY HAVING AT LEAST ONE UNFILTERED FEEDTHROUGH

(75) Inventors: Rajesh V. Iyer, Eden Prairie, MN (US); Daniel J. Koch, Lakeville, MN (US); Simon E. Goldman, St. Louis Park, MN (US); Shawn D. Knowles, St. Francis, MN (US); William J. Taylor, Anoka, MN (US); Joyce K. Yamamoto, Maple Grove, MN (US); Gregory J. Haubrich, Champlin, MN (US); Michael Nowak, Andover, MN (US); David Nghiem, Shoreview, MN (US); Roger L. Hubing, Hastings, MN (US); Len D. Twetan, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 470 days.

(21) Appl. No.: 11/343,106

(22) Filed: Jan. 30, 2006

(65) Prior Publication Data
US 2007/0179554 A1    Aug. 2, 2007

(51) Int. Cl.
*A61N 1/00*    (2006.01)
*H03H 7/00*    (2006.01)
(52) U.S. Cl. .............................. 607/37; 607/36; 333/182
(58) Field of Classification Search .................... 607/37, 607/36; 333/182; 82/37
See application file for complete search history.

(56) References Cited

U.S. PATENT DOCUMENTS

| | | | | |
|---|---|---|---|---|
| 3,961,294 A * | 6/1976 | Hollyday | | 333/182 |
| 5,620,476 A | 4/1997 | Truex et al. | | |
| 5,683,435 A | 11/1997 | Truex et al. | | |
| 5,759,197 A * | 6/1998 | Sawchuk et al. | | 607/36 |
| 5,870,272 A | 2/1999 | Seifried et al. | | |
| 5,942,842 A * | 8/1999 | Fogle, Jr. | | 313/313 |
| 5,951,595 A * | 9/1999 | Moberg et al. | | 607/37 |
| 6,044,302 A * | 3/2000 | Persuitti et al. | | 607/37 |
| 6,052,623 A * | 4/2000 | Fenner et al. | | 607/36 |
| 6,240,317 B1 * | 5/2001 | Villaseca et al. | | 607/60 |
| 6,414,835 B1 | 7/2002 | Wolf et al. | | |
| 6,428,368 B1 * | 8/2002 | Hawkins et al. | | 439/271 |
| 6,459,935 B1 * | 10/2002 | Piersma | | 607/37 |
| 6,482,154 B1 | 11/2002 | Haubrich et al. | | |
| 6,519,133 B1 * | 2/2003 | Eck et al. | | 361/302 |
| 6,566,978 B2 * | 5/2003 | Stevenson et al. | | 333/182 |

(Continued)

FOREIGN PATENT DOCUMENTS

EP    1695736 A    8/2006

(Continued)

OTHER PUBLICATIONS

International Search Report, PCT/US2007/060611, May 22, 2007, 5 Pages.

*Primary Examiner* — Nicole F Lavert

(57) ABSTRACT

An implantable medical device is provided including a housing, an external circuit element extending outwardly from the housing, an internal circuit enclosed by the housing, a feedthrough array disposed along the housing having at least one filtered feedthrough and at least one unfiltered feedthrough, wherein the unfiltered feedthrough is adapted for connection to the outwardly extending circuit element; and including means for minimizing electromagnetic coupling between the filtered feedthrough and the unfiltered feedthrough.

32 Claims, 14 Drawing Sheets

U.S. PATENT DOCUMENTS

| | | | |
|---|---|---|---|
| 6,586,675 B1 * | 7/2003 | Bealka et al. | 174/50.56 |
| 6,660,116 B2 | 12/2003 | Wolf et al. | |
| 6,765,780 B2 * | 7/2004 | Brendel et al. | 361/302 |
| 6,874,423 B2 * | 4/2005 | Heeke | 102/202.12 |
| 6,882,248 B2 * | 4/2005 | Stevenson et al. | 333/182 |
| 7,046,499 B1 * | 5/2006 | Imani et al. | 361/302 |
| 7,274,963 B2 * | 9/2007 | Spadgenske | 607/36 |
| 2002/0027484 A1 * | 3/2002 | Stevenson et al. | 333/182 |
| 2003/0139096 A1 * | 7/2003 | Stevenson et al. | 439/620 |
| 2004/0012462 A1 * | 1/2004 | Kim | 333/182 |
| 2004/0215280 A1 * | 10/2004 | Dublin et al. | 607/36 |
| 2005/0203584 A1 | 9/2005 | Twetan et al. | |
| 2006/0009813 A1 | 1/2006 | Taylor et al. | |

FOREIGN PATENT DOCUMENTS

| | | | |
|---|---|---|---|
| EP | 1695736 A1 * | 8/2006 | |
| GB | 2127629 A * | 4/1984 | |
| WO | WO9741923 A | 11/1997 | |

* cited by examiner

METHOD AND APPARATUS FOR MINIMIZING EMI COUPLING IN A FEEDTHROUGH ARRAY HAVING AT LEAST ONE UNFILTERED FEEDTHROUGH

TECHNICAL FIELD

The invention relates generally to implantable medical devices and more particularly to a feedthrough array including at least one unfiltered feedthrough.

BACKGROUND

Electrical feedthroughs provide an electrical circuit path extending from the interior of a hermetically sealed housing of an implantable medical device (IMD) to the exterior of the housing. IMDs, such as cardiac pacemakers, implantable cardiovertor defibrillators, neuromuscular stimulators, and physiological monitors, employ such electrical feedthroughs to make electrical connection with leads, electrodes or sensors located outside the IMD housing. A conductive path is provided through the feedthrough by a conductive feedthrough pin which is electrically insulated from the IMD housing. IMDs commonly operate in association with multiple leads, electrodes or sensors and thus feedthrough arrays including multiple feedthroughs have been developed.

IMDs can be susceptible to electromagnetic interference (EMI), which can interfere with proper IMD function. As such, capacitive filter arrays have been incorporated in the feedthrough arrays to filter each of the feedthroughs, shunting EMI at the entrance to the IMD. Examples of capacitive filtered feedthroughs for use with an IMD are generally disclosed in commonly assigned U.S. Pat. No. 5,870,272 (Seifried et al.) and U.S. Pat. No. 6,414,835 (Wolf, et al.), both of which patents are incorporated herein by reference in their entirety.

IMDs are typically provided as programmable devices having RF telemetry circuitry adapted for bidirectional communication with an external programmer or monitor. Telemetry transmission systems commonly used with IMDs have typically relied upon the generation of low amplitude magnetic fields. Current oscillating in an LC circuit of an RF telemetry antenna in a transmitting mode induces currents in a closely spaced RF telemetry antenna in a receiving mode. An RF carrier frequency in some IMD products is set at a relatively low frequency of 175 kHz. The external RF telemetry antenna and the IMD RF telemetry antenna, which is typically enclosed within the IMD housing, are brought into close proximity with the use of a programming head.

Use of a telemetry system that requires a programming head limits the retrieval and transmission of data from/to an IMD to times when the patient can be positioned close to the programmer and the patient or other personnel are available for holding the programming head over the IMD. It has been recognized that distance telemetry systems that would allow telemetric communication between an IMD and external programmer or monitor over a distance of several meters, without the use of a programming head, is desirable. Telemetry sessions could occur while a patient is active, for example performing an exercise test or going about normal daily activities. A clinician performing tests or reprogramming the IMD could be freed of the task of maintaining the position of the programming head, making it easier for him/her to perform other tasks.

A distance or long-range telemetry system is generally disclosed in U.S. Pat. No. 6,482,154 issued to Haubrich et al. A distance telemetry system will transmit using high frequency RF signals, for example using UHF signals, between an antenna in a receiving mode and an antenna in a transmitting mode. Such systems utilize an IMD RF telemetry antenna that is located outside the IMD housing. The antenna is coupled to IMD circuitry, enclosed within the IMD housing, through an antenna feedthrough. Since the antenna feedthrough needs to conduct the telemetry RF signals into the IMD during telemetry sessions, the antenna feedthrough does not significantly filter the desired high frequency signals.

Cross-talk could occur between the unfiltered antenna feedthrough and any filtered feedthroughs included in the IMD. Such cross-talk would interfere with normal device sensing of signals on the filtered feedthroughs, potentially leading to inappropriate function of the IMD. In order to minimize EMI coupling that could occur across an unfiltered feedthrough and any filtered feedthroughs inside the IMD, a separate unfiltered feedthrough could be provided along the IMD housing, at a different location than a filtered feedthrough array. However, providing separate filtered and unfiltered feedthrough assemblies would likely increase IMD manufacturing complexity and/or cost. As IMD technology has advanced, the physical size of IMDs has decreased and the number of electrodes and sensors used with some IMDs has increased. As such, the physical space available for providing a separate unfiltered feedthrough is limited.

DETAILED DESCRIPTION

In the following description, references are made to illustrative embodiments for carrying out the invention. It is understood that other embodiments may be utilized without departing from the scope of the invention. In the description, the term "inwardly," when used with regard to a feedthrough assembly, generally refers to a direction toward the interior of an IMD. The term "outwardly" generally refers to a direction toward the exterior of an IMD.

Figure 1:
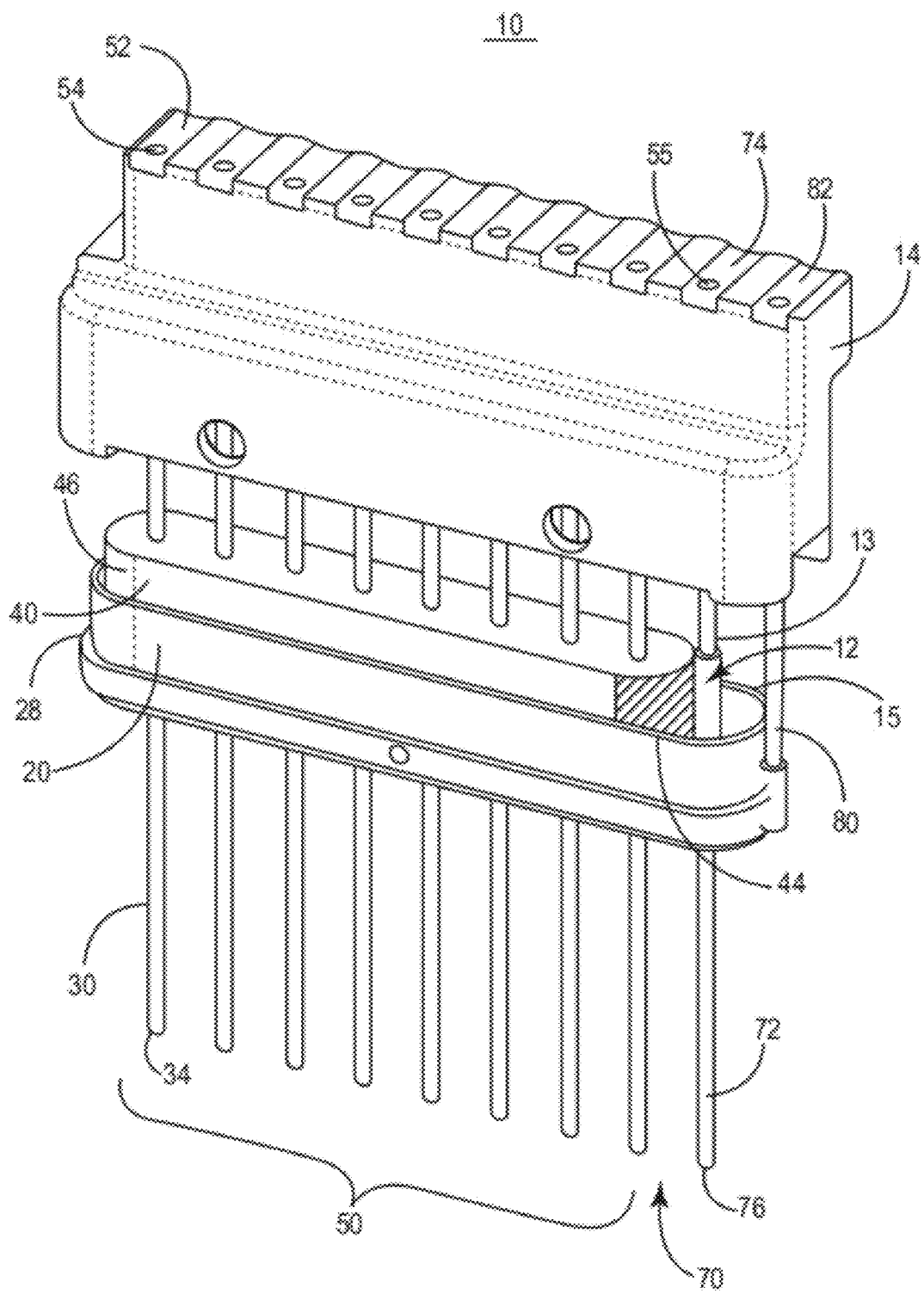
FIG. 1 is a perspective view of a feedthrough array, including at least one unfiltered feedthrough, according to one embodiment of the invention.

FIG. 1 is a perspective view of a feedthrough array, including at least one unfiltered feedthrough, according to one embodiment of the invention. Feedthrough array 10 includes a ferrule 20, a capacitor array 40, an electronics module assembly (EMA) 14, multiple filtered feedthroughs 50, at least one unfiltered feedthrough 70, and a ground line 80. Each filtered feedthrough 50 includes an electrically conductive feedthrough pin 30 extending through ferrule 20 and capacitive filter array 40. Unfiltered feedthrough 70 includes an electrically conductive feedthrough pin 72 extending through ferrule 20. Unfiltered feedthrough pin 72 does not extend through capacitive filter array 40. In one embodiment of the invention, unfiltered feedthrough pin 72 is provided with an electromagnetic shield member 12 for preventing or minimizing electrical cross-talk between unfiltered feedthrough 70 and filtered feedthroughs 50.

As used herein, the term "unfiltered feedthrough" refers to a feedthrough intended to pass RF telemetry signals or other desired high frequency signals without significant filtering or attenuation of the desired RF signals. It is recognized that the unfiltered feedthrough may inherently filter some undesired signal frequencies or may be designed to filter unwanted signal frequencies in the form of a band pass, high pass or low pass filter which passes the desired RF signals. In contrast, filtered feedthroughs generally filter a broad range of signal frequencies, primarily acting as low pass filters that significantly attenuate RF signals in the range that are passed by the unfiltered feedthrough.

Shield member 12 is shown as a generally cylindrical member having an inner surface 13 forming a lumen through which unfiltered feedthrough pin 72 extends. Shield member 12 may be formed of any non-conductive material having a relatively low dielectric constant to thereby provide electrical shielding between filtered feedthroughs 50 and unfiltered feedthrough 70 without filtering high-frequency RF signals that may be carried by unfiltered feedthrough pin 72. For example, a material may be selected for fabricating shield member 12 having a dielectric constant in the range of about 1 to 10, although materials having a dielectric constant greater than 10 may be used successfully in some applications and are not outside the intended scope of the invention. Examples of appropriate materials from which shield member 12 may be fabricated include poly ether ketone (PEEK), other low dielectric polymer materials, glass, quartz, and pyrex.

Shield member 12 is provided with a conductive metallic coating on its outer surface 15. Outer surface 15 may be coated using a sputtering process or any other metallization technique. In one embodiment, shield member outer surface 15 is sputtered with a combination of titanium/gold. Among the appropriate metals that may be used to coat outer surface 15 are titanium, tantalum, niobium, platinum, iridium, silver, gold and any combinations or alloys thereof, though other metals, alloys or combinations, or other conductive materials such as semi-conductors, or a conductive epoxy, may be used.

Capacitor array 40 is typically terminated by the capacitor manufacturer by applying a metal coating on each capacitor inner surface and outer surface 46. This coating typically includes silver or silver-palladium mixes with glass frit and an organic binder-solvent mix. A conductive metallic material may be sputtered on the terminated surfaces (inner capacitor surfaces and outer surface 46) of capacitor array 40 to reduce contact resistances on the capacitor surfaces. In some embodiments, a capacitor filter array end 44, positioned adjacent unfiltered feedthrough 70, is provided with a metallic coating to provide shielding between unfiltered feedthrough 70 and filtered feedthroughs 50. A metallic coating may be applied to capacitor filter array end 44 using sputtering or any other metallization technique to build-up metallic material on capacitor array end 44. Examples of appropriate metals include those listed above for metallizing the outer surface 15 of shield member 12.

Ferrule 20 is typically laser welded to an IMD housing. Ferrule 20 may be provided with a welding flange 28 to facilitate welding of ferrule 20 to the IMD housing when ferrule 20 is placed in a housing opening. Ferrule 20 is typically formed of a conductive metal such as niobium, titanium, titanium alloys, platinum, molybdenum, zirconium, tantalum, vanadium, tungsten, iridium, rhodium, rhenium, oxmium, ruthenium, palladium, silver, and alloys, mixtures and combinations thereof. Ferrule 20 may be hermetically joined to an IMD housing by other welding methods, or even soldered or glued. Ground line 80 is electrically and mechanically coupled to ferrule 20 providing a ground path to the IMD housing.

The outwardly extending portion 34 of filtered feedthrough pin 30 is generally connected to electrical circuitry, connectors, or contacts located outside the IMD housing, for example disposed within an IMD connector header. Filtered feedthrough pin 30 may alternatively be connected directly to a connector on a medical lead. The outer portion 76 of unfiltered feedthrough pin 72 is likewise coupled to electrical circuitry, a connector, or contact located outside the IMD housing. In one embodiment, unfiltered feedthrough pin 72 is coupled to an RF telemetry antenna located outside an IMD housing.

EMA 14 is typically provided as a molded component fabricated from a polymeric material such as Ultem, acetal, polysulphone, polycarbonate, polypropylene, Teflon or similar plastic materials. EMA 14 includes multiple, electrically conductive contact pads 52 corresponding to the number of filtered feedthroughs included in feedthrough array 10. Each contact pad 52 is provided with an aperture 54 through which a filtered feedthrough pin 30 may extend. EMA 14 further includes a contact pad 74 corresponding to each unfiltered feedthrough 70, having an aperture 55 for extending unfiltered feedthrough pin 72 there through. Contact pad 82 is provided for electrical and mechanical coupling to ground line 80.

During assembly, EMA 14 is slid down over capacitive filter array 40 and ferrule 20 such that each filtered feedthrough pin 30, unfiltered feedthrough pin 72, and ground line 80 extend through a respective EMA aperture. Each filtered feedthrough pin 30, unfiltered feedthrough pin 72, and ground line 80 are then electrically coupled to a respective contact pad 52 by brazing, welding or using a conductive adhesive or epoxy. Any remaining length of the feedthrough pins 30 and 72 and ground line 80 may be trimmed. Contact pads 52 are used for electrically coupling each filtered feedthrough 30, unfiltered feedthrough 70, and ground line 80 to IMD internal circuitry.

Figure 2:
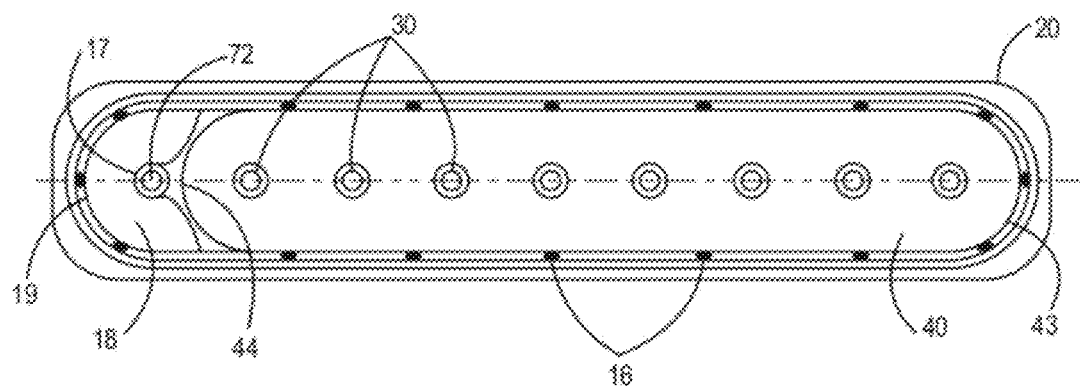
FIG. 2 is a top view of an alternative embodiment of a feedthrough array.

FIG. 2 is a top view of an alternative embodiment of a feedthrough array. Shield member 18 is provided as a generally "C-shaped" member having an inner surface 17 forming an open lumen through which unfiltered feedthrough pin 72 may extend. Outer surface 19 of shield member 18 is provided with a metallic coating as described above. A C-shaped shield member 18 in combination with a metallized capacitor array end 44 may provide adequate shielding between filtered feedthrough pins 30 and unfiltered feedthrough pin 72 to prevent or minimize electromagnetic coupling across the filtered feedthrough pins 30 and unfiltered feedthrough pin 72.

It is recognized that an electrical shield member through which unfiltered conductor pin 72 extends may be provided in various shapes and geometries and is not limited to the generally cylindrical or C-shaped geometries shown in FIGS. 1 and 2. For example, an electrical shield member may be provided with a generally oval, square, rectangular, U-shaped, D-shaped, or other cross-sectional geometry.

Conductive joints 16 are formed at discreet locations between the outer surface 43 of capacitive filter array 40 and ferrule 20 and between shield member outer surface 19 and ferrule 20. Conductive joints 16 may be formed using a conductive adhesive, such as conductive epoxy, conductive polyimide or solder connection. Conductive joint 16 serves to connect the outer surface 43 of the capacitor array 40 (ground potential) to ferrule 20. Conductive joints 16 serve to minimize the effects of inductive impedance through the feedthrough array. In alternative embodiments, a continuous conductive joint may be formed, for example by applying a continuous bead of a conductive adhesive or solder, along the junction of outer surface 43 of capacitive filter array 40 and ferrule 20 and along the junction of shield member outer surface 19 and ferrule 20. Conductive joints 16 may alternatively be formed by creating a braze joint, weld joint, solder joint, or other electrically conductive joint.

Figure 3:
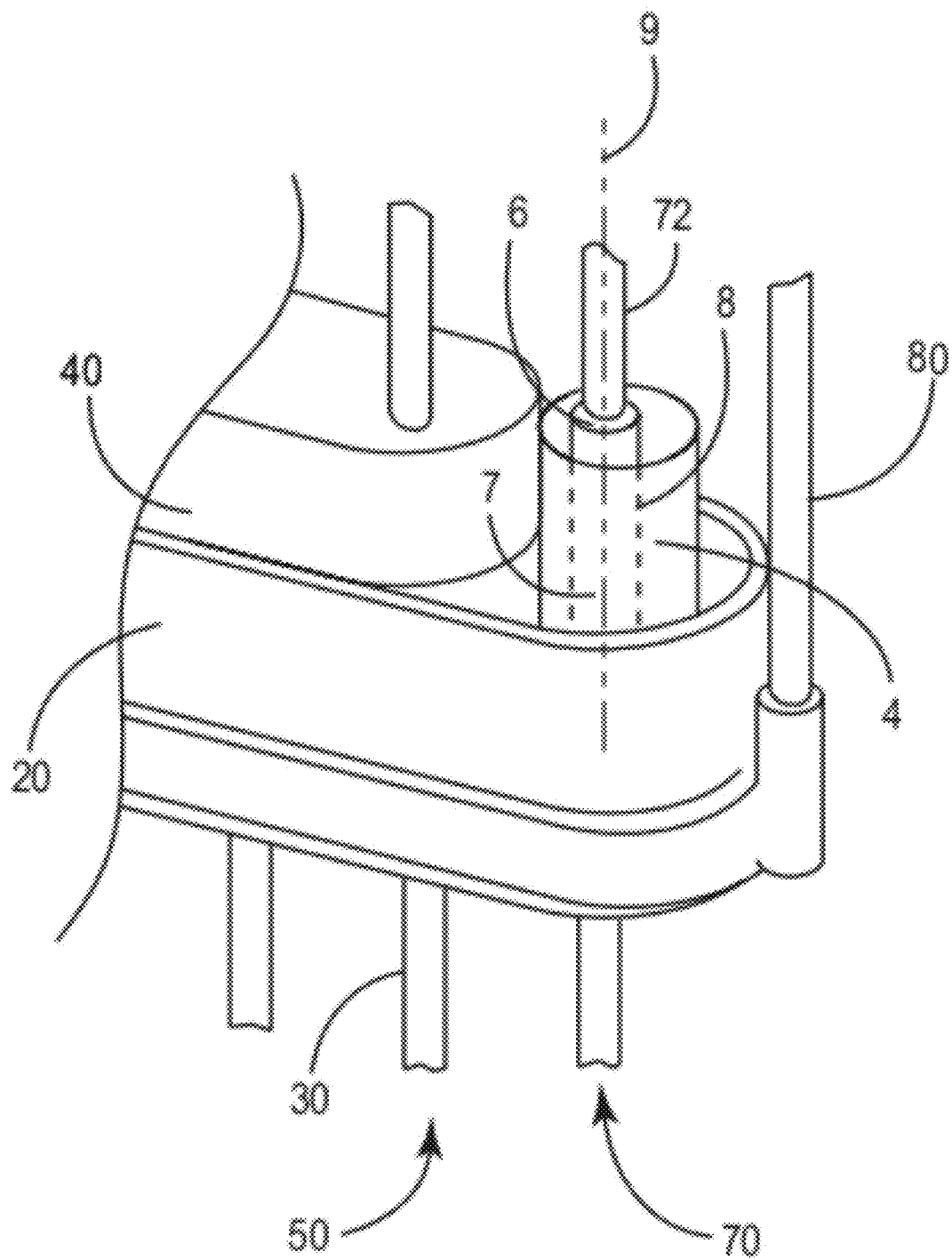
FIG. 3 is a partial perspective view of another embodiment of a feedthrough array.

FIG. 3 is a partial perspective view of another embodiment of a feedthrough array. Electrical shield member 4 is shown as a generally cylindrical member having an inner surface 6 forming a feedthrough pin lumen 7. The center axis 9 of feedthrough pin lumen 7 and the central axis 8 of shield member 4 are not co-axial. It is understood that an unfiltered feedthrough pin lumen 7 may be located along any axis extending through shield member 4.

Figure 4:
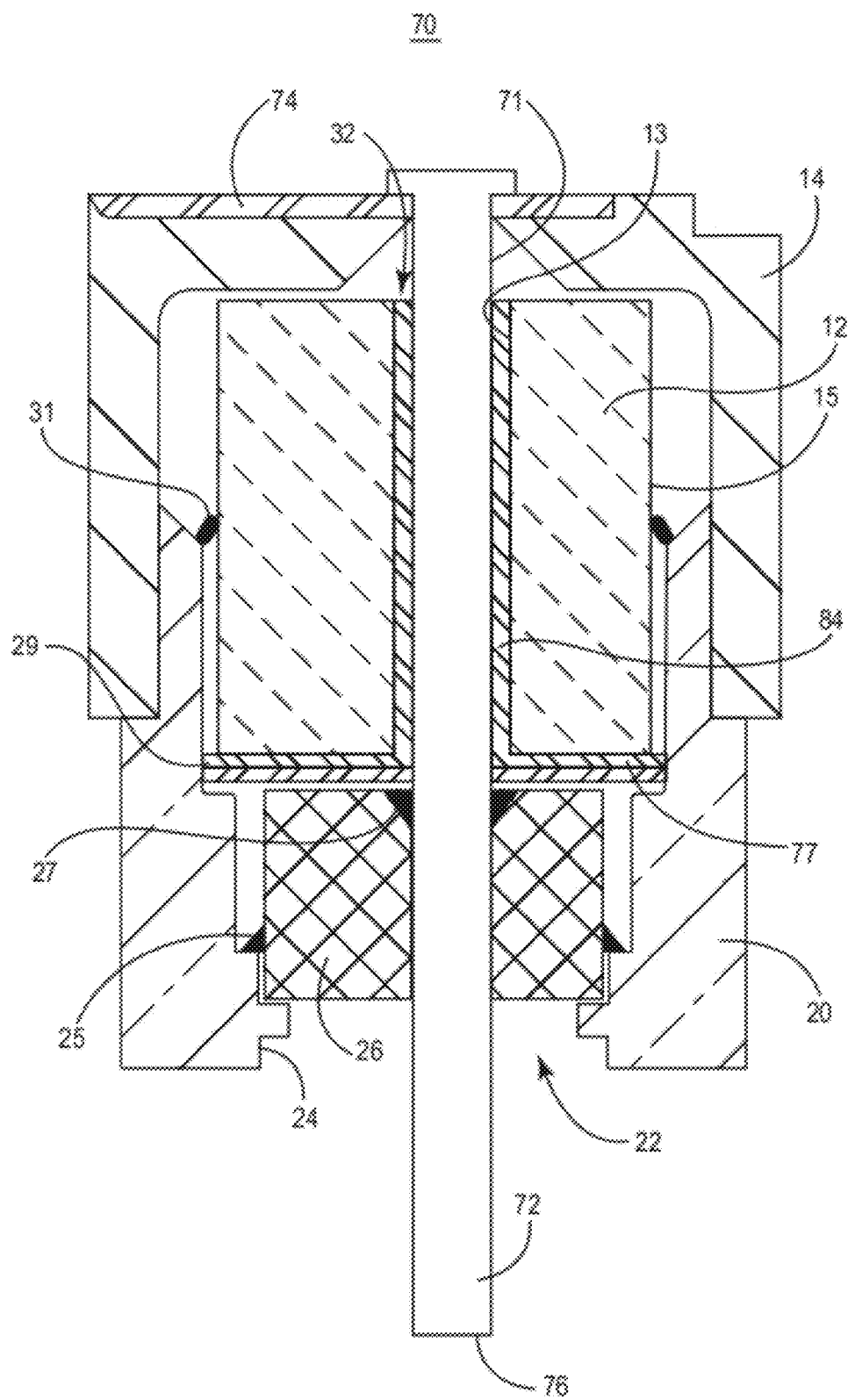
FIG. 4 is a sectional view of an unfiltered feedthrough according to one embodiment of the invention.

FIG. 4 is a sectional view of an unfiltered feedthrough according to one embodiment of the invention. Unfiltered feedthrough pin 72 extends through an aperture 22 formed by an inner surface 24 of ferrule 20. An insulating seal member 26 is positioned in aperture 22 for insulating unfiltered feedthrough pin 72 from ferrule 20 and for providing a hermetic seal along unfiltered feedthrough 70. Insulating seal member 26 may be formed from ceramic, glass, or other low dielectric, insulating materials. Insulating seal member 26 is coupled to ferrule 20 at joint 25. Unfiltered feedthrough pin 72 is coupled to insulating seal member 26 at joint 27. Joints 25 and 27 may be brazed, welded or glued joints.

Electrical shield member 12 is positioned along unfiltered feedthrough pin 72. An insulator 29 is optionally provided between shield member 12 and insulating seal member 26. Insulator 29 may be formed from polyimide, other insulating polymeric material, ceramic or glass. Inner surface 13 of shield member 12 forms an unfiltered feedthrough pin lumen 32 that is sized such that the inner surface 13 of shield member 12 is located at a spaced-apart distance 84 from the outer diameter surface 71 of unfiltered feedthrough pin 72. In one embodiment the spaced-apart distance 84 is air filled. In another embodiment, spaced-apart distance 84 is filled or partially filled with a non-conductive adhesive such as a non-conductive epoxy. A non-conductive adhesive may also be applied between outwardly extending shield end 77 and insulator 29. Insulator 29 provides a barrier against the flow of non-conductive adhesive into joint 27 when the adhesive is applied in spaced-apart distance 84. Joint 27 is typically subjected to leak testing to ensure the integrity of the hermetically sealed device. Adhesive flowing into joint 27 may mask manufacturing flaws of joint 27.

As described previously, shield member outer surface 15 is metallized and is electrically and mechanically coupled to ferrule 20 at joint 31. Joint 31 may be formed using a conductive adhesive, such as a conductive epoxy or polyimide, or by welding, soldering, or brazing. The EMA 14 is positioned over unfiltered feedthrough pin 72, shield member 12, and ferrule 20. Unfiltered feedthrough pin 72 is electrically coupled to contact pad 74. EMA 14 is sealed to ferrule 20 using non-conductive adhesive (e.g., epoxy, polyimide or glue) A hermetically sealed, shielded, unfiltered feedthrough 70 is thereby provided for use in a feedthrough array that includes filtered feedthroughs with a minimum of cross-talk between the unfiltered and filtered feedthroughs.

In some embodiments, shield member 12 is designed to perform as a transmission line by selecting the low-dielectric material and conductive coating so as to provide input impedance matching between unfiltered feedthrough 70 and an external antenna, or other lead, circuit, or connector, coupled to unfiltered feedthrough pin 72.

Figure 5:
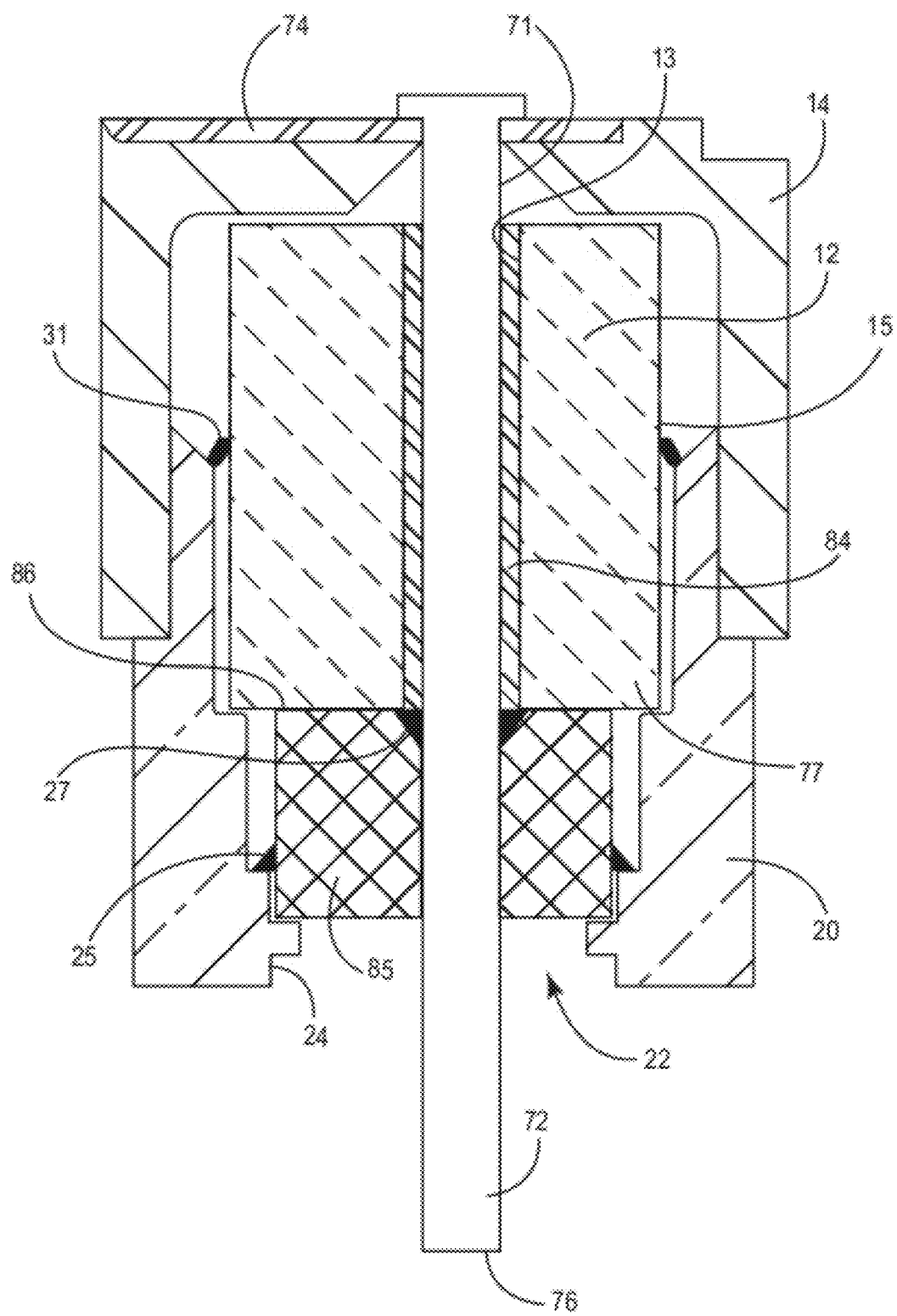
FIG. 5 is a sectional view of an unfiltered feedthrough according to an alternative embodiment.

FIG. 5 is a sectional view of an unfiltered feedthrough according to an alternative embodiment. Insulating seal 85 is fabricated from glass. The inwardly extending end 86 of insulating seal 85 is bonded to the outwardly extending end 77 of shield member 12.

Figure 6:
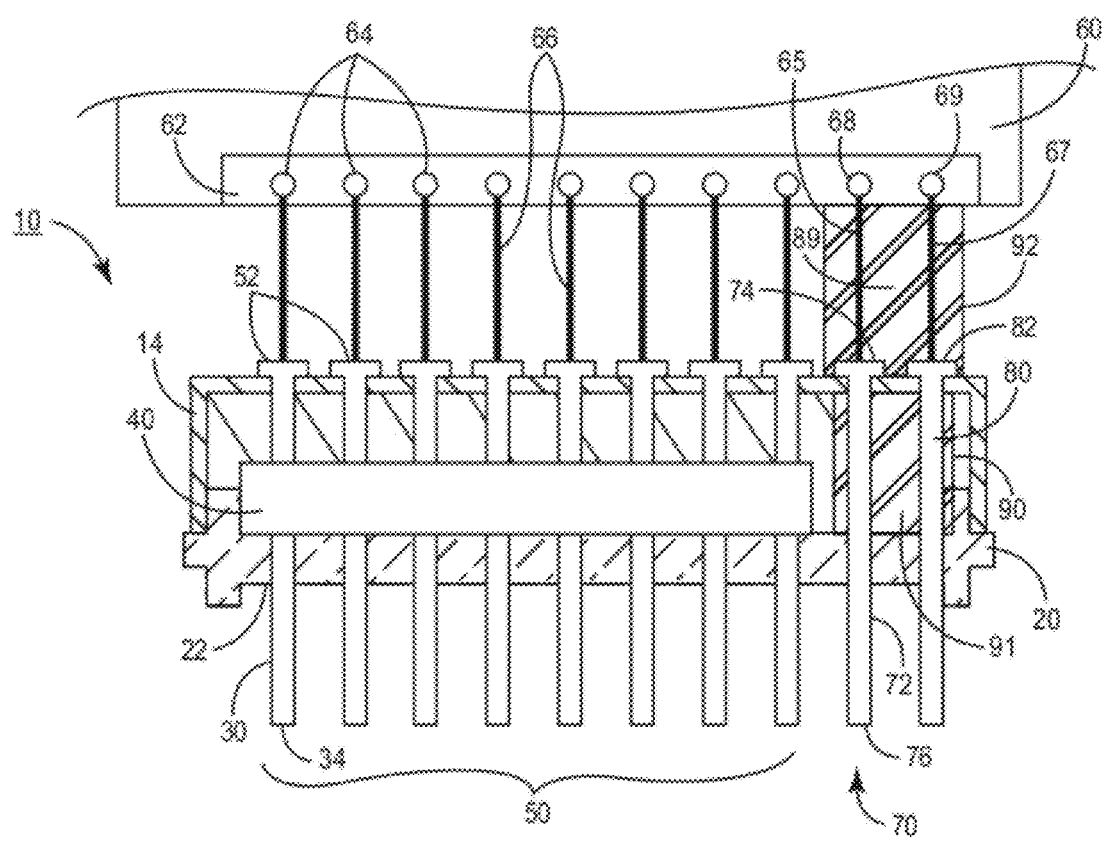
FIG. 6 is a sectional view of a feedthrough array including at least one unfiltered feedthrough according to another embodiment of the invention.

FIG. 6 is a sectional view of a feedthrough array including at least one unfiltered feedthrough according to another embodiment of the invention. Electrically conductive ferrule 20 is configured for placement within an opening of an IMD housing. Ferrule 20 includes multiple, insulated apertures 22 to accommodate multiple filtered feedthroughs 50 and at least one unfiltered feedthrough 70. Each filtered feedthrough pin 30 extends through a ferrule aperture 22 and capacitive filter array 40.

Capacitive filter array 40 generally includes discoidal, multi-layer ceramic capacitors, which may be generally cylindrical in shape. At least one active capacitor electrode is formed within the filter substrate extending outward from the filtered feedthrough 50 in overlapping spaced relation to at least one common ground plate. The number of capacitor active and ground electrodes, the size of each, and the dielectric spacing and overlapping relation can be varied in accordance with the capacitance value and voltage rating of the capacitor, which can vary between IMD applications. In operation, the capacitive filter array 40 permits relatively low frequency electrical signals to be conducted along filtered feedthroughs 50 while shielding and decoupling/attenuating undesired interference signals of relatively high frequency. Examples of filtered feedthroughs are generally described in the above-incorporated U.S. Pat. No. 5,870,272 (Seifried, et al.) and U.S. Pat. No. 6,414,835 (Wolf, et al.).

Feedthrough array 10 includes at least one unfiltered feedthrough 70 including unfiltered feedthrough pin 72 extending inwardly from ferrule 20 to unfiltered feedthrough contact pad 74. Unfiltered feedthrough 70 allows relatively high frequency signals to be conducted from outside the IMD housing to internal circuitry 60. In one embodiment unfiltered feedthrough pin 72 and groundline 80, shown schematically in FIG. 6, are incorporated in a shielded conductor 90, which may be embodied, for example, as a coaxial cable, strip line conductor, or microstrip line conductor. Shielded conductor 90 includes unfiltered feedthrough pin 72, embodied as at least one active conductor, and ground line 80, embodied as at least one ground conductor, spaced apart by an insulating, low-dielectric layer 91. Shielded conductor 90 is electrically and mechanically coupled to unfiltered feedthrough contact pad 74 and a ground line contact pad 82.

Filtered feedthrough contact pads 52, unfiltered contact pad 74, and ground line contact pad 82 are electrically coupled to internal IMD circuitry 60 using laser ribbon or wire bonding, soldering, welding, laser welding, brazing, gluing or other suitable coupling methods. Each filtered contact pad 52 is electrically coupled to an individual button connector 64 included in a button array 62 on IMD internal circuitry 60 via a conductor 66. Likewise, unfiltered contact pad 74 and ground line contact pad 82 are coupled to unfiltered button connector 68 and ground line button connector 69, respectively, via individual conductors 65 and 67.

A second shielded conductor 92, which may also be embodied as a coaxial cable, strip line conductor, or microstrip line conductor, may be provided in addition to or alternatively to shielded conductor 90. Shielded conductor 92 is provided for coupling unfiltered feedthrough contact pad 74 and ground line contact pad 82 to IMD internal circuitry 60. Shielded conductor 92 includes at least one active unfiltered conductor 65 which is electrically coupled between unfiltered contact pad 74 and unfiltered button connector 68 on IMD internal circuitry 60. Shielded conductor 92 further includes at least one ground line conductor 67, which is electrically coupled to ground line contact pad 82 and ground line button connector 69. A low-dielectric insulator 89 is provided between unfiltered conductor 65 and ground line conductor 67.

In various embodiments, shielded conductor 90 may be grounded to ferrule 20 at its outwardly extending end, grounded to ground line contact pad 82 at its inwardly extending end, or coupled to a separately provided ground line anywhere along its length. In some embodiments, the ground conductor of shielded conductor 90 may be grounded at its outwardly extending end to ferrule 20 and left floating at its inwardly extending end. Conversely, the ground conductor of shielded conductor 90 may be left floating at its outwardly extending end and grounded at its inwardly extending end, for example to ground line contact pad 82 or to the ground conductor of shielded conductor 92. Likewise, the ground conductor of shielded conductor 92 may be left floating at either its outwardly extending end or its inwardly extending end. The ground conductor of shielded conductor 92 may be grounded at its outwardly extending end to the ground conductor of shielded conductor 90 or to ferrule 20 and/or grounded at its inwardly extending end to the ground of IMD internal circuitry 60, for example along ground line button connector 69. To provide the most effective shielding, both the inwardly extending and outwardly extending ends of both shielded conductor 90 and shielded conductor 92 are appropriately grounded. Although, it is contemplated that in some embodiments, the ground conductors at both inwardly extending and outwardly extending ends of shielded conductor 90 and shielded conductor 92 may be left floating. While ground line 80 and ground line conductor 67 are shown schematically as distinct elements in FIG. 6, it is to be understood, as described above, that the ground line 80 and ground line conductor 67 may be incorporated in shielded conductors 90 and 92 as the inactive or ground conductor provided in a shielded conductor structure.

Furthermore, shielded conductor 90 and shielded conductor 92 may be embodied as transmission line structures designed to match the impedance of an electrical circuit, antenna, lead or other electrical component coupled to outwardly extending end 76 of unfiltered feedthrough pin 72.

Figure 7:
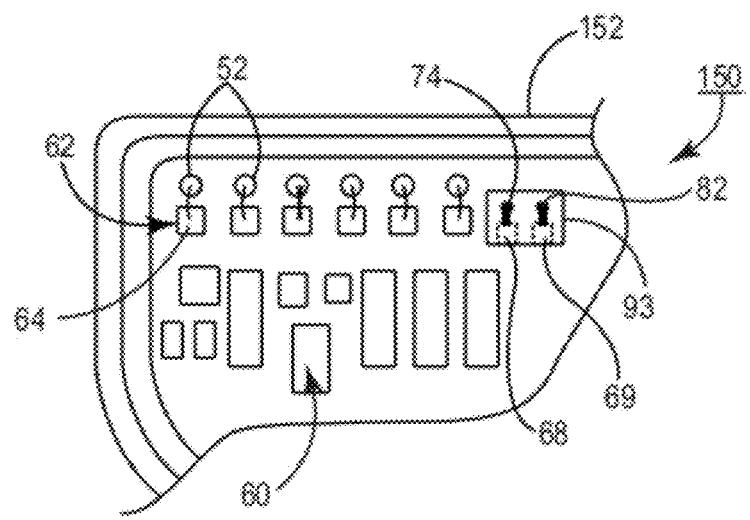
FIG. 7 is a partial, top open view of an IMD.

FIG. 7 is a partial, top open view of an IMD 150. IMD 150 includes a hermetically sealed housing 152 enclosing internal circuitry 60, which is typically in the form a hybrid circuit board. Internal circuitry 60 includes a button array 62 with multiple button connectors 64 for electrically connecting filtered feedthrough contact pads 52 to internal circuitry 60. A shielded conductor 93 is used to couple unfiltered feedthrough contact pad 74 to button connector 68 of button array 62. Shielded conductor 93 includes a ground line conductor which is coupled from ground line contact pad 82 to ground line button connector 69.

Figure 8:
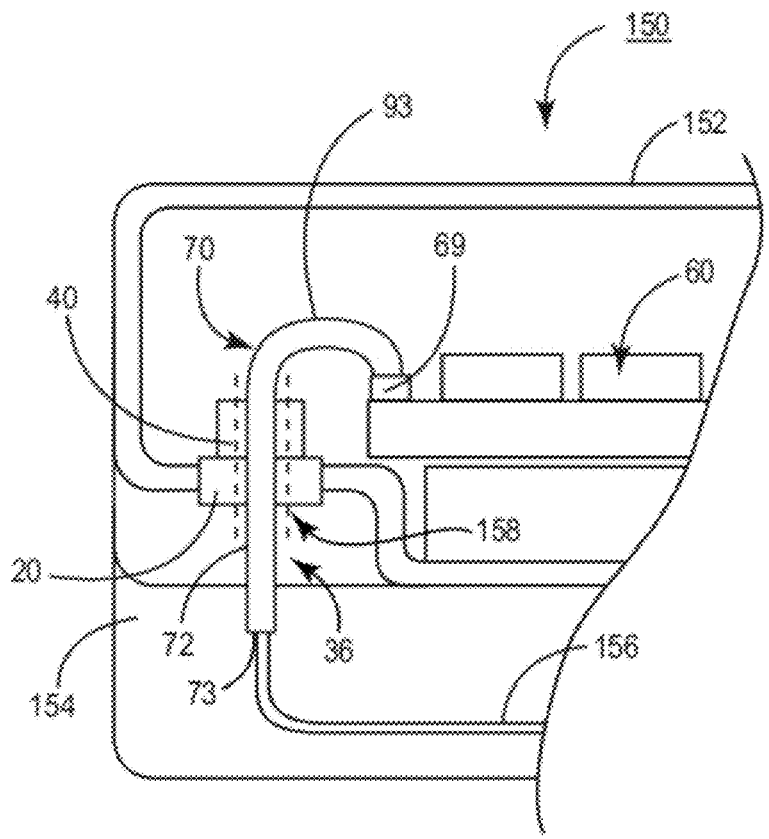
FIG. 8 is a partial, side sectional view of an IMD.

FIG. 8 is a partial, side sectional view of an IMD. IMD 150 includes hermetically sealed housing 152 and a connector header 154 positioned along housing 150. Feedthrough array 36 is shown with ferrule 20 positioned in an opening of housing 152. Unfiltered feedthrough pin 72 extends from outside housing 152 inwardly through ferrule 20. Feedthrough pin 72 is incorporated in a shielded conductor 93 that is electrically coupled to internal circuitry 60. Shielded conductor 93 includes a ground conductor that is coupled to ground line button connector 69 and/or to IMD housing 152 via ferrule 20. In one embodiment, the outwardly extending portion 76 of unfiltered feedthrough pin 72 is electrically and mechanically coupled to an antenna 156 incorporated in connector header 154. Antenna 156 is used for sending and receiving relatively high frequency RF signals during telemetry sessions between IMD 150 and an external device. Antenna 156 may be embodied as generally disclosed in U.S. Pat. Appl. Pub. No. 2005/0203584 (Twetan, et al.), hereby incorporated herein by reference in its entirety.

By including a shielded conductor 93 along at least a portion of unfiltered feedthrough 70, the radiating length of unfiltered feedthrough 70 is reduced or eliminated. The shielded conductor 93 reduces RF coupling between unfiltered feedthrough 70 and any of the filtered feedthroughs included in a feedthrough array. Shielded conductor 93 further minimizes radiation of RF signals to filtered feedthroughs and IMD internal circuitry 60. In the embodiment shown in FIG. 8, the antenna feedpoint 158 is located at the junction between the unfiltered feedthrough pin 72 and shielded conductor 93. By moving the feedpoint 158 away from the filtered feedthroughs and IMD internal circuitry 60, interference due to high-frequency signals carried by unfiltered feedthrough 70 is minimized.

Figure 9:
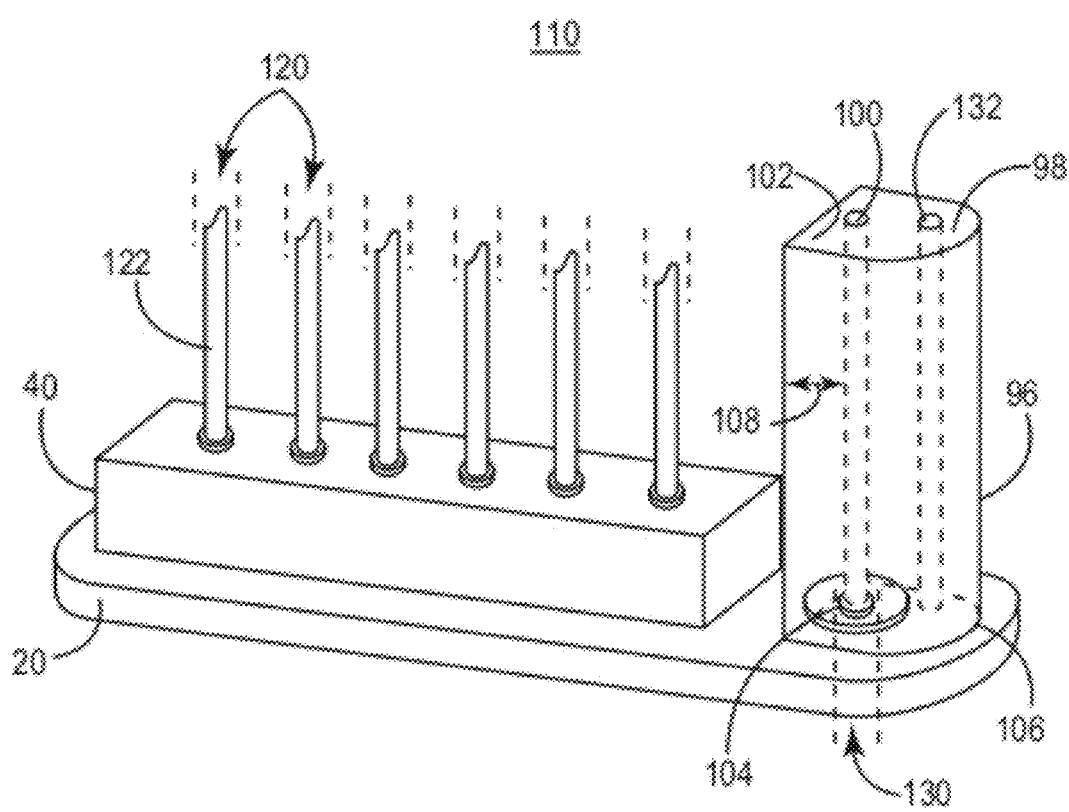
FIG. 9 is a perspective view of an alternative embodiment of a feedthrough array including a shielded, unfiltered feedthrough.

FIG. 9 is a perspective view of an alternative embodiment of a feedthrough array including a shielded, unfiltered feedthrough. Feedthrough array 110 is shown having multiple filtered feedthroughs 120, an unfiltered feedthrough 130 and ground line 132. Each filtered feedthrough 120 includes a filtered feedthrough pin 122 extending inwardly through ferrule 20 and through a capacitive filter array 40.

Unfiltered feedthrough 130 includes an unfiltered feedthrough pin 100 extending through an insulated aperture 104 of ferrule 20. Ground line 132 is provided as a conductive pin electrically and mechanically coupled to ferrule 20. Unfiltered feedthrough 130 and ground line 132 are enclosed by a metallic shield 96 extending inwardly from ferrule 20. Metallic shield 96 is mechanically and electrically coupled to ferrule 20 and is disposed around unfiltered feedthrough pin 100 and ground line 132 such that an inner surface 102 of metallic shield 96 is positioned at a spaced apart distance 108 from unfiltered feedthrough pin 100 and ground line 132. Metallic shield 96 may be fabricated from any conductive metal including, but not limited to, gold, silver, titanium, nickel, tantalum, and niobium. Metallic shield 96 may be coupled to ferrule 20 at joint 106 by brazing, soldering, welding or gluing. Metallic shield 96 may alternatively or additionally be grounded to ground line 132 along any portion of the length of shield 96.

A low-dielectric, insulator 98 may be enclosed between the inner surface 102 of metallic shield 96 and unfiltered feedthrough pin 100. Alternatively, metallic shield 96 may use an air dielectric filling the distance 108 between metallic shield 96 and unfiltered feedthrough pin 100 and ground line 132. Shield 96 may extend to a button array provided on IMD internal circuitry (shown in FIG. 7). Shield 96 may be electrically coupled to a ground plate included in IMD internal circuitry using conductive adhesive, welding, soldering or other appropriate joining method. When the inwardly extending end of metallic shield is appropriately grounded to the IMD internal circuitry and the outwardly extending end of metallic shield 96 is appropriately grounded to ferrule 20, a separate ground line 132 may not be required.

Figure 10:
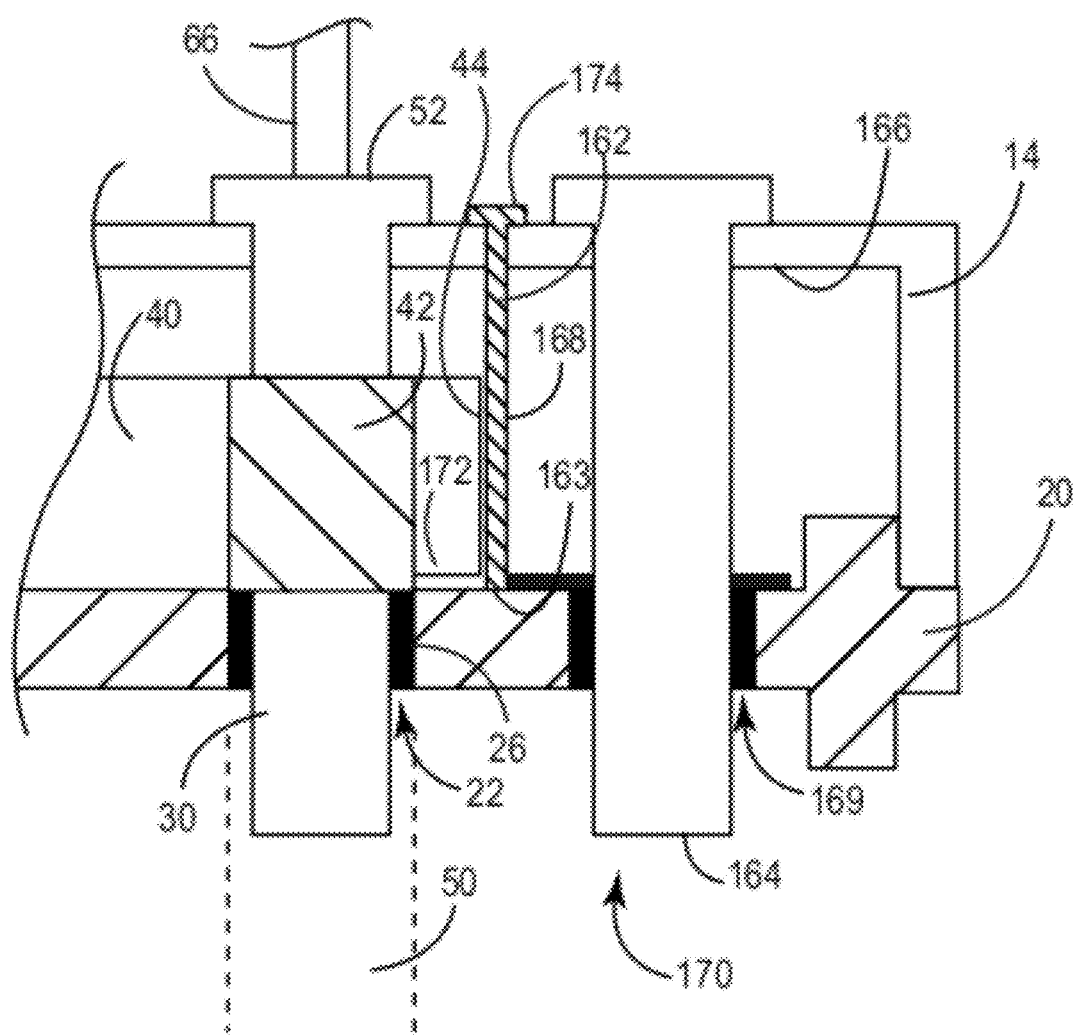
FIG. 10 is a partial, side sectional view of an alternative embodiment of a feedthrough array having an unfiltered feedthrough.

FIG. 10 is a partial, side sectional view of an alternative embodiment of a feedthrough array 160 having an unfiltered feedthrough 170. An unfiltered feedthrough pin 164 is shown extending inwardly through insulated aperture 168 of ferrule 20. A filtered feedthrough pin 30 extends inwardly through insulated aperture 22, through a capacitive filter 42 of capacitive filter array 40 and is electrically and mechanically coupled to contact pad 52. A conductor 66 is used to couple contact pad 52 to a button connector included in IMD internal circuitry.

Capacitor filter array 40 includes an end surface 44 facing unfiltered feedthrough pin 164. Feedthrough array 160 includes shield plate 162 extending inwardly from ferrule 20, along end surface 44 of capacitor array 40. Shield plate 162 provides shielding of filtered feedthrough 50 from RF signals that may be radiating from unfiltered feedthrough pin 164. Shield plate 162 has a side surface 168 facing unfiltered feedthrough 170. Shield plate 162 is coated with an insulating material on side surface 168 to increase high voltage breakdown. Shield plate 162 may be fabricated from any conductive metal or metal alloy, for example tantalum, titanium, silver, niobium, gold or alloys thereof. An insulating coating applied to shield plate 162 may be any insulating polymer coating such as non-conductive epoxy, polyimide, polyethylene, paralyne, PEEK, Teflon, or a ceramic coating such as titanium oxide.

Shield plate 162 is electrically coupled to ferrule 20 at joint 163, which may be a brazed, welded, or soldered joint or formed using a conductive adhesive. Shield plate 162 may be coupled to capacitor ground line 172 and thereby serve as a ground path for capacitor array 40. Shield plate 162 may extend through EMA 14 and provide a ground line contact pad 174 for coupling to IMD internal circuitry. Alternatively, a separate ground line may be provided as described previously and shield plate 162 may be terminated at outwardly facing inner surface 166 of EMA 14.

Figure 11A:
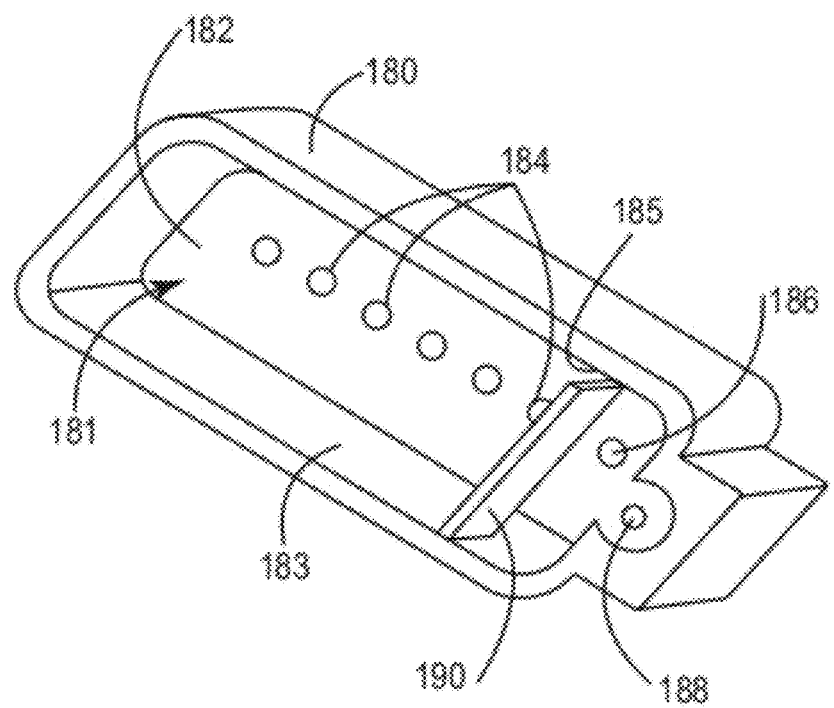
FIG. 11A is a perspective view of one embodiment of an electronics module assembly including a shield member for use in a feedthrough array including at least one unfiltered feedthrough.

FIG. 11A is a perspective view of one embodiment of an EMA including a shield member for use in a feedthrough array including at least one unfiltered feedthrough. EMA 180 includes opposing sidewalls 183 and 185 separated by a top side 181 having an inner surface 182. EMA 180 includes multiple apertures 184 positioned along top side 181 for accommodating a like number of filtered feedthrough pins. EMA 180 further includes an unfiltered feedthrough pin aperture 186 and a ground line aperture 188 in top side 181.

A shield plate 190 extends outwardly from inner surface 182, between EMA sidewalls 183 and 185. Shield plate 190 is positioned along outwardly facing inner surface 182 at a location between unfiltered aperture 186 and the nearest, adjacent filtered feedthrough aperture 184. Shield plate 190 may be fabricated as a part of EMA 180 or may be produced as a separate component that is press fit or bonded to EMA 180. When fabricated as part of EMA 180, shield plate 190 may be formed from the same polymeric material as EMA then coated with any metallic coating, along at least the surface facing an unfiltered feedthrough pin extending through aperture 186, and coupled to ground. Alternatively, shield plate 190 is made from a conductive metallic material, with or without an insulating coating, inserted in EMA 180, and coupled to ground. Appropriate shield plate materials and insulating coatings, if used, are listed above in conjunction with FIG. 10. Shield plate 190 could also be fabricated from an RF gasket, for example a beryllium copper gasket. In addition to providing a grounded metallic coating on the surface of shield plate 190, the inner sidewalls 183 and 185 of EMA 180 may be metallized, at least along the portion of sidewalls 183 and 185 that will be adjacent the unfiltered feedthrough pin extending through aperture 186 (to the right of shield plate 190 in FIG. 11A).

Figure 11B:
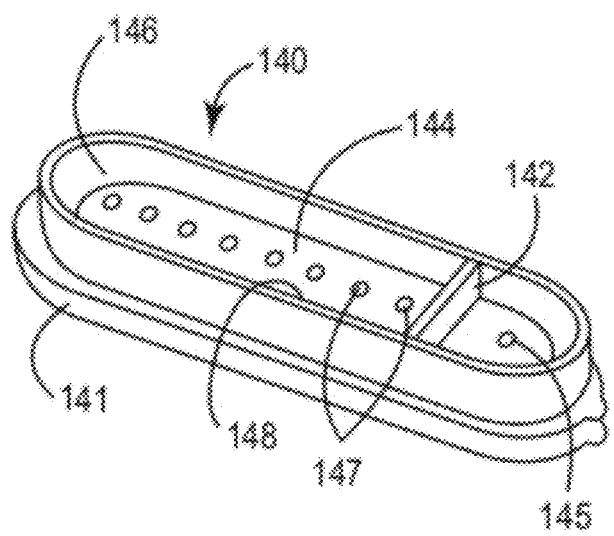
FIG. 11B is a perspective view of a ferrule including a shield plate.

FIG. 11B is a perspective view of a ferrule including a shield plate. In an alternative design, a shield plate 142 is fabricated as part of ferrule 140 and used to isolate the filtered feedthroughs from the unfiltered feedthrough. Ferrule 140 includes opposing inner sidewalls 146 and 148 separated by inner surface 144 of ferrule bottom 141. At least one, insulated filtered feedthrough pin aperture 147 and at least one insulated, unfiltered feedthrough pin aperture 145 are provided extending through ferrule bottom 141. Shield plate 142 extends inwardly from inner surface 144, between inner sidewalls 146 and 148. Shield plate 142 is positioned along inner surface 144 such that shield plate 142 separates unfiltered feedthrough pin aperture 145 from the nearest adjacent filtered feedthrough pin aperture 147. Shield plate 142 thereby minimizes RF coupling between the filtered feedthrough pin(s) and the unfiltered feedthrough pin(s) extending through ferrule 140 after using ferrule 140 in a feedthrough array assembly.

Shield plate 142 is generally fabricated from the same metallic material as ferrule 140, however shield plate 142 may be fabricated from any conductive metallic material, with or without an insulating coating. Shield plate 142 may be fabricated as part of ferrule 140 or as a separate piece part that is electrically and mechanically coupled to ferrule 140, for example by welding, soldering, or using a conductive adhesive.

When a feedthrough array is assembled using EMA 180 (shown in FIG. 11A), shield plate 190 will extend between a filtered feedthrough and an unfiltered feedthrough, from EMA inner surface 182 to the ferrule shield plate 142. Ferrule shield plate 142 and EMA shield plate 190 may be adapted to be mechanically coupled and electrically grounded to each other. EMA shield plate 190 thereby provides RF shielding between a filtered and unfiltered feedthrough within the EMA portion of the feedthrough array and ferrule shield plate 142 provides shielding within the ferrule portion of the feedthrough array. In alternative embodiments, the shield plate 190 included in EMA 180 may be dimensioned such that it extends from the inner surface 182 of EMA 180 to the inner surface 144 of ferrule 140 when the feedthrough array is assembled. Shield plate 190 may then be grounded to ferrule

140. Alternatively, ferrule shield plate 142 may be dimensioned such that it extends from inner surface 144 of ferrule 140 to top side inner surface 182 of EMA 180. The inner side walls 183 and 185 of EMA 180 adjacent the unfiltered feedthrough may be metallized and grounded to the shield plate 190 or 142 as described previously. It is recognized that numerous configurations for providing and implementing a shield plate between the unfiltered feedthrough and filtered feedthroughs may be conceived.

Figure 12:
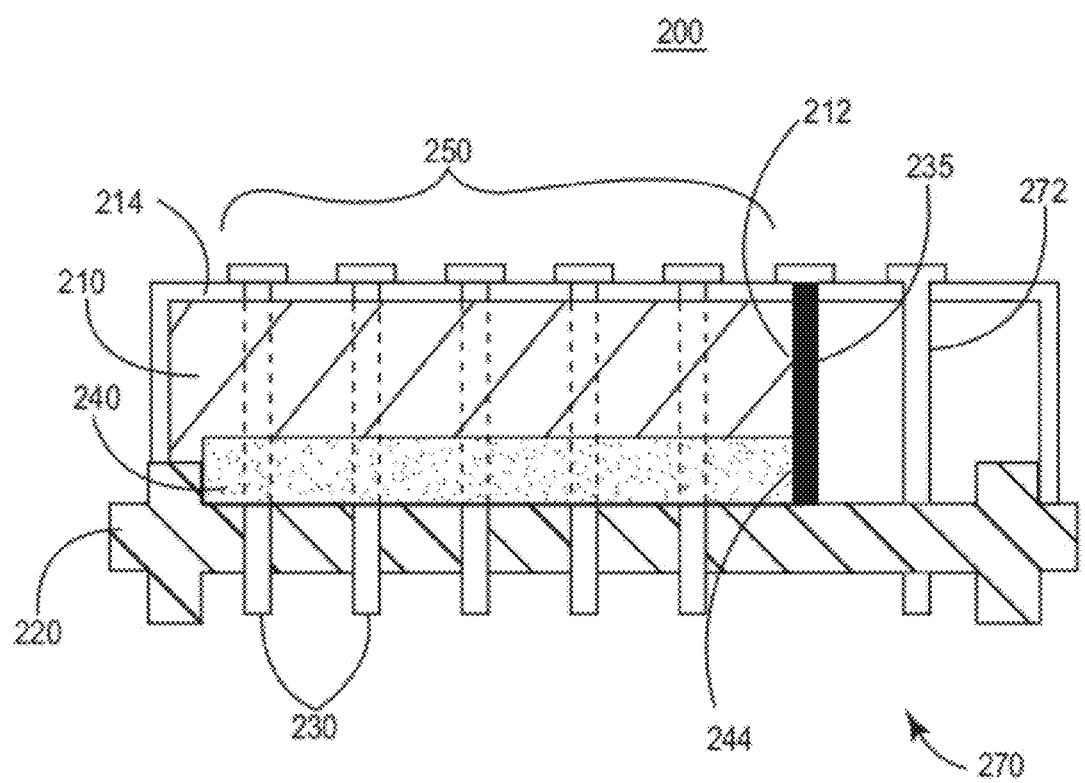
FIG. 12 is a side, sectional view of a feedthrough array including a filtered feedthrough shielding manifold according to an alternative embodiment of the invention.

FIG. 12 is a side, sectional view of a feedthrough array including a filtered feedthrough shielding manifold according to an alternative embodiment of the invention. Feedthrough array 200 includes multiple filtered feedthroughs 250 and at least one unfiltered feedthrough 270. Unfiltered feedthrough 270 includes a feedthrough pin 272 extending inwardly through ferrule 220 and EMA 214. Filtered feedthroughs 250 each include a feedthrough pin 230 extending inwardly through ferrule 220, a capacitive filter array 240, shielding manifold 210 and EMA 214. Shielding manifold 210 is fabricated from a dielectric material, such as a ceramic, and provides RF shielding to filtered feedthrough pin 230 extending therethrough, within EMA 14. End surface 212 of manifold 210, which is adjacent to unfiltered feedthrough 270, may be provided with a conductive coating. For example, manifold end surface 212 may be metal plated or sputtered.

Feedthrough array 200 may optionally include a shield plate 235 extending along an end surface 212 of shielding manifold 210 and/or an end surface 244 of capacitor array 240 to provide additional shielding between unfiltered feedthrough 270 and filtered feedthroughs 250. Shield plate 235 may be coupled to capacitor array ground and serve as a ground line of feedthrough array 200 as described previously. Alternatively, a separate ground line may be provided.

Figure 13:
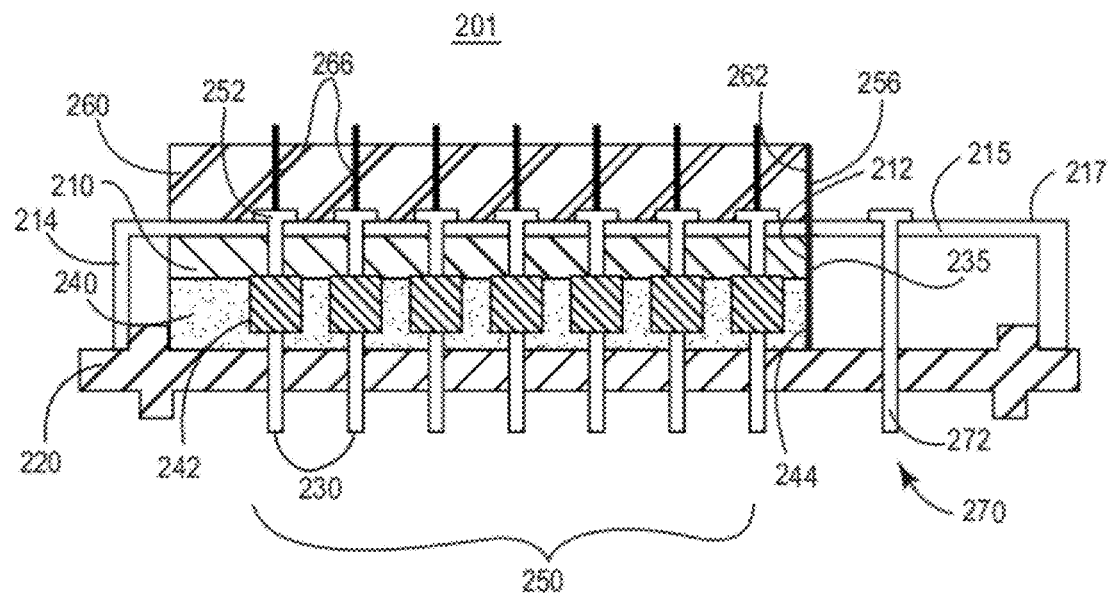
FIG. 13 is a side, sectional view of a feedthrough array including a second shielding manifold.

FIG. 13 is a side, sectional view of a feedthrough array including a second shielding manifold. Feedthrough array 201 includes multiple filtered feedthroughs 250 each including feedthrough pin 230 extending through ferrule 220, a capacitive filter 242 of capacitive filter array 240, internal shielding manifold 210, EMA 214 and external shielding manifold 260. Internal shielding manifold 210 corresponds to identically numbered shielding manifold shown in FIG. 12 which provides RF shielding to filtered feedthrough pins 230 within EMA 214. External shielding manifold 260 is formed from a dielectric material, such as a ceramic, is coupled to the outer surface 217 of EMA top side 215. External shielding manifold 260 may be coupled to EMA 214 by brazing, welding, soldering, gluing or other appropriate method. External shielding manifold 260 provides RF shielding to conductors 266 used to couple filtered contact pads 252 to IMD internal circuitry. External shielding manifold 260 may be designed to extend along any portion of the length of filtered feedthrough conductors 266.

A shield plate 256 may extend along an end surface 262 of external shielding manifold 260, end surface 212 of internal shielding manifold 210, and end surface 244 of capacitor array 240. Shield plate 256 thus extends between filtered feedthroughs 250 and unfiltered feedthrough 270 (including pin 272), providing electromagnetic shielding. Shield plate 256 may also serve as a ground line as described previously. Alternatively, external shielding manifold end surface 262 may coated with a conductive coating, such as a metal plated or metal sputtered coating.

Figure 14:
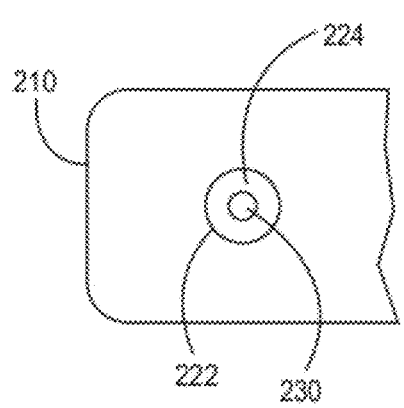
FIG. 14 is a partial top view of one embodiment of a shielding manifold.

FIG. 14 is a partial top view of one embodiment of a shielding manifold. Shielding manifold 210 includes an inner surface 222 forming a feedthrough pin lumen 224 through which a filtered feedthrough pin extends. During feedthrough array assembly, each filtered feedthrough pin 30 is threaded through a respective feedthrough pin lumen 224.

Figure 15:
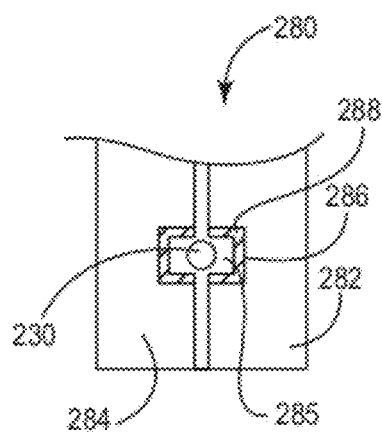
FIG. 15 is a partial top view of an alternative embodiment of a shielding manifold.

FIG. 15 is a partial top view of an alternative embodiment of a shielding manifold. Shielding manifold 280 includes a right manifold half 282 and a left manifold half 284 which form a feedthrough pin lumen 285 when the right half 282 and left half 284 are interfaced as shown in FIG. 15. During feedthrough array assembly, each filtered feedthrough pin 230 is positioned along a respective feedthrough pin lumen 285 in one of the right or left manifold halves 282 or 284. The opposite manifold half 282 or 284 is then placed over the first half. The two halves 282 and 284 are joined in a sealing, bonding, gluing, or other appropriate process.

As illustrated by FIG. 15, a shielding manifold feedthrough pin lumen is not limited to a generally circular cross-section as shown in FIG. 14. Feedthrough pin lumens may be provided having any cross-sectional geometry as long as the lumens are of adequate size to allow filtered feedthrough pins 230 to extend there through.

In FIG. 15, feedthrough pin lumen 285 formed by inner wall 286 is provided with a ferrite lining 288. Ferrite lining 288 acts to suppress high frequency electromagnetic radiation thereby providing additional RF isolation to feedthrough pin 230.

Figure 16:
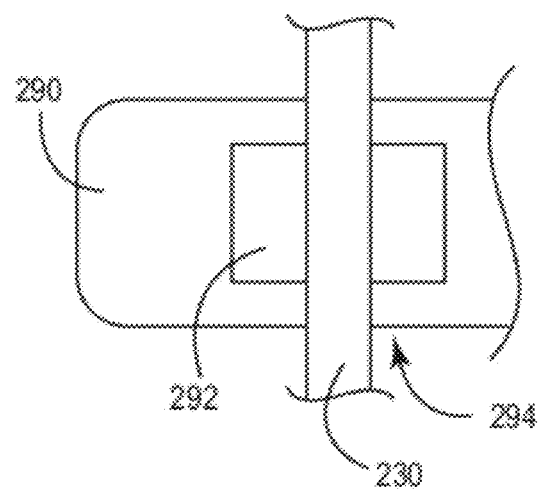
FIG. 16 is a partial side, sectional view of a shielding manifold including embedded capacitive filters.

FIG. 16 is a partial side, sectional view of a shielding manifold 290 including embedded capacitive filters. Shielding manifold 290 is provided with multiple feedthrough pin lumens 294 for carrying a filtered feedthrough pin 230 for each of a corresponding number of filtered feedthroughs. A capacitive filter 292 may be embedded in shielding manifold 290 to provide additional high-frequency filtering of signals carried by filtered feedthrough pin 230. In the embodiments shown in FIG. 13, either or both of external shielding manifold 260 and internal shielding manifold 210 may be provided as a shielding manifold incorporating embedded capacitive filters. Such embedded capacitive filters are typically discoidal filters and may be embodied as generally disclosed, for example, in U.S. Pat. No. 5,870,272 (Seifried et al.). The capacitor ground lead(s) of embedded capacitive filter 292 may be coupled to a shield plate 256 (shown in FIG. 13) serving as a ground line or a separately provided ground line.

Figure 17:
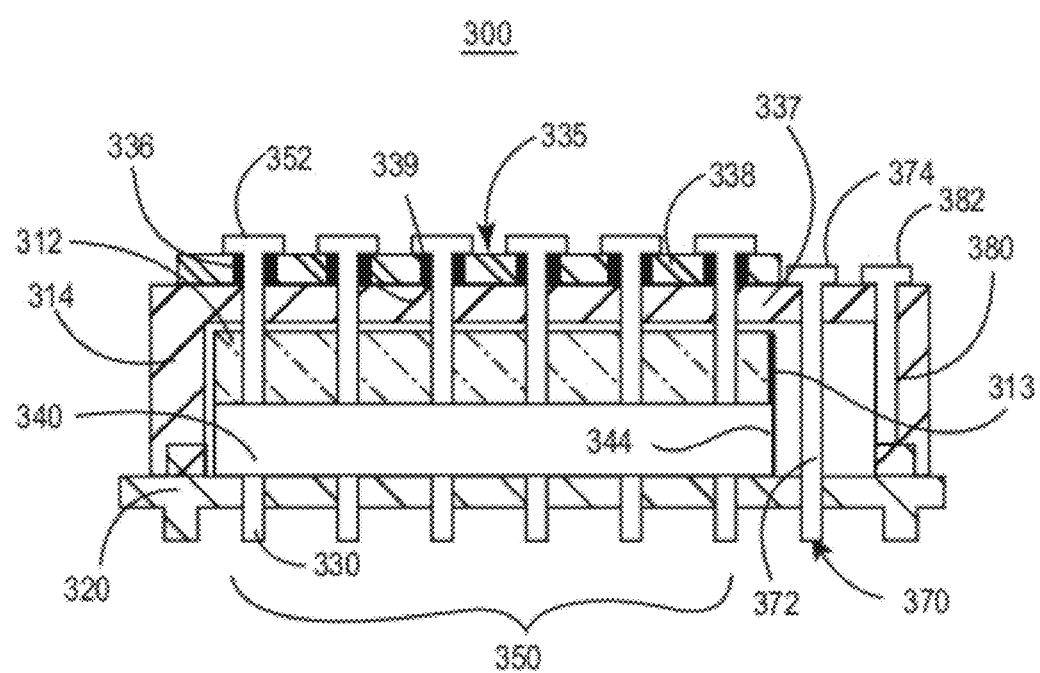
FIG. 17 is yet another embodiment of a feedthrough array including a filtered contact pad substrate for shielding filtered contact pads from an unfiltered contact pad.

FIG. 17 is yet another embodiment of a feedthrough array including a filtered contact pad substrate for shielding filtered contact pads from an unfiltered contact pad. Feedthrough array 300 includes multiple filtered feedthroughs 350. Each filtered feedthrough 350 includes a filtered feedthrough pin 330 extending through ferrule 320, capacitive filter array 340, an optional shielding manifold 312, and EMA 314. Filtered contact pads 352 are formed on a contact pad shield 335. Contact pad shield 335 includes a dielectric substrate 338, such as a ceramic substrate, for shielding filtered contact pads 352 from EMI. The end surface 337 of contact pad shield 335, which faces unfiltered feedthrough 370 approximately adjacent contact pad 374 of unfiltered feedthrough pin 372, may be metallized. Any of shielding manifold end surface 313 and capacitor array end surface 344 may also be metallized.

Contact pad shield 335 may further include embedded capacitive filters 336 to provide additional high-frequency filtering of signals conducted through filtered contact pads 352. Accordingly, bottom surface 339 of contact pad shield 335 is metallized to provide a ground path from embedded capacitive filters 336 to ground line 380. Contact pad 382 is provided for electrical and mechanical coupling to ground line 380.

Figure 18:
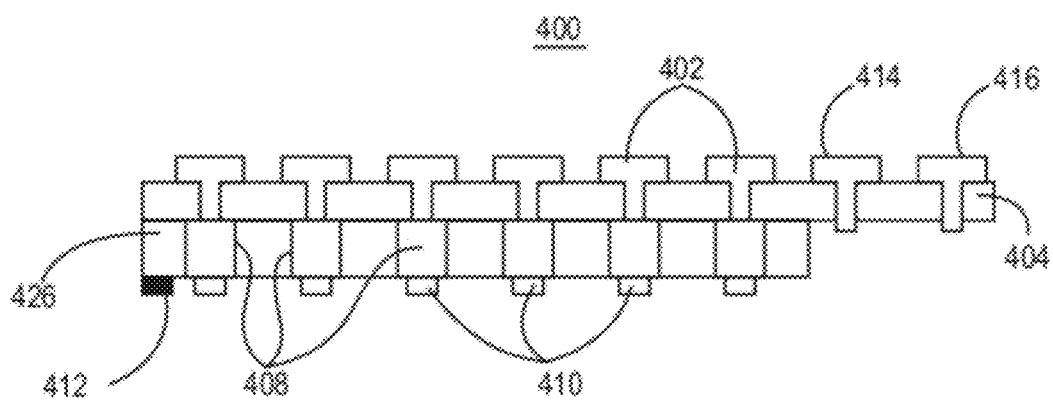
FIG. 18 is a side view of a button array used for electrically coupling a feedthrough array to IMD internal circuitry.

FIG. 18 is a side view of a button array 400 used for electrically coupling a feedthrough array to IMD internal circuitry. Button array 400 includes multiple filtered button connectors 402 for electrically coupling a conductor extending from a filtered feedthrough contact pad included in a feedthrough array. Button array 400 further includes an unfiltered button connector 414 for electrically coupling a conductor extending from an unfiltered feedthrough contact pad in the feedthrough array. Likewise, a ground line button connector 416 is provided for electrically coupling a conductor extending from a ground line contact pad in the feedthrough array.

Each of the button connectors 402, 414 and 416 extend through a circuit board substrate 404 to provide through connections for wiring to IMD internal circuitry via conductors 410. Filtered button connectors 402 additionally extend through a button array shield 406. Button array shield 406 is formed from a dielectric material to provide EMI shielding of filtered button connectors 402. Button array shield 406 may further include embedded capacitive filters 408 to provide high-frequency filtering of signals conducted through filtered button connectors 402. Button array shield 406 includes a surface mount ground connection 412. Alternatively, or additionally, button array shield may include ferrite or a ferrite-loaded material.

Thus, a feedthrough array including both filtered and unfiltered feedthroughs for use in an IMD has been presented in the foregoing description with reference to specific embodiments. In the various embodiments, different shielding configurations or combinations of shielding configurations have been described for minimizing or preventing EM coupling across filtered feedthroughs and unfiltered feedthroughs and/or minimizing radiation of RF signals from an unfiltered feedthrough to other IMD components. Electromagnetic shielding configurations may be implemented in various embodiments for shielding any portion of an unfiltered feedthrough and/or a filtered feedthrough including the feedthrough pins, the contact pads, the conductors coupled between contact pads and button connectors, and the button connectors. It is appreciated that various modifications to the referenced embodiments may be made without departing from the scope of the invention as set forth in the following claims.

The invention claimed is:

1. A feedthrough array, comprising:
   an electrically conductive ferrule having an inner surface forming an aperture;
   at least one filtered feedthrough extending through the ferrule and electrically insulated from the ferrule;
   at least one unfiltered feedthrough comprising a conductive pin extending through the ferrule aperture and electrically insulated from the ferrule, the conductive pin comprising a first portion extending within the ferrule aperture and a second portion extending from the first portion; and
   means for minimizing electromagnetic coupling between the filtered feedthrough and the unfiltered feedthrough comprising a shield member having an electrically-grounded, conductive surface and extending along the second portion between the filtered and the unfiltered feedthroughs at a spaced apart distance from the second portion.

2. The feedthrough array of claim 1 wherein the means for minimizing electromagnetic coupling includes an insulating surface between the electrically grounded conductive surface and the second portion of the unfiltered feedthrough pin.

3. The feedthrough array of claim 1 wherein the shield member includes a generally cylindrical insulating member having an inner surface forming a feedthrough pin lumen and the electrically-grounded, conductive surface comprises an outer surface of the insulating member coated with a conductive coating.

4. The feedthrough array of claim 3 wherein the shield member is designed to function as a transmission line having an input impedance matching an impedance of a component coupled to an outwardly extending end of the unfiltered feedthrough pin.

5. The feedthrough array of claim 1, wherein means for minimizing electromagnetic coupling further comprises an insulator extending within the spaced apart distance between the conductive surface and the second portion.

6. The feedthrough array of claim 1, further comprising an insulating seal positioned in the aperture, and wherein the shield member includes an outwardly facing end surface positioned along the insulating seal, and further including an insulator disposed between the outwardly facing end surface of the shield member and the insulating seal.

7. The feedthrough array of claim 1, further comprising an insulating seal positioned in the aperture, and wherein the shield member includes an outwardly extending end surface bonded to the insulating seal.

8. The feedthrough array of claim 3 wherein the insulating member is provided with a generally C-shaped cross-section.

9. The feedthrough array of claim 1 wherein the shield member comprises a metallic material having an inner surface located at the spaced-apart distance from the unfiltered feedthrough pin and an insulative coating on the inner surface.

10. The feedthrough array of claim 1, wherein the means for minimizing electromagnetic coupling further comprises an insulating layer extending between the conductive surface and the second portion of the unfiltered feedthrough pin along the spaced-apart distance and comprising an adhesive to couple an inner surface of the insulating layer to the unfiltered feedthrough pin.

11. The feedthrough array of claim 3 wherein the generally cylindrical member includes a central axis and the feedthrough pin lumen is positioned off the central axis.

12. The feedthrough array of claim 1, further comprising a capacitive filter array, the at least one filtered feedthrough extending through the capacitive filter array, the filter array having an end surface adjacent the unfiltered feedthrough and wherein the electrically-grounded, conductive surface extends between the end surface and the unfiltered feedthough.

13. The feedthrough array of claim 1, further comprising a capacitive filter array having an outer surface, the at least one filtered feedthrough extending through the capacitive filter array, and further including means for minimizing the effects of inductive impedance comprising a conductive joint extending along an inner surface of the ferrule and at least one of an outer surface of the shield member and an outer surface of the capacitive filter array.

14. The feedthrough array of claim 1 wherein the means for minimizing electromagnetic coupling comprises a shielded conductor extending along the second portion toward internal circuitry enclosed in a hermetically sealed housing, the shielded conductor comprising the unfiltered feedthrough pin second portion as an active conductor.

15. The feedthrough array of claim 1 wherein the means for minimizing electromagnetic coupling includes a metallic shield extending inwardly from the electrically conductive ferrule along the second portion of the unfiltered feedthrough pin between the unfiltered feedthrouqh and the at least one filtered feedthrough.

16. The feedthrough array of claim 1 the means for minimizing electromagnetic coupling includes a shield plate electrically coupled to the ferrule and extending inwardly therefrom, between the filtered feedthrough and the unfiltered feedthrough.

17. The feedthrough array of claim 16 wherein the shield plate includes a side surface facing the unfiltered feedthrough and the side surface is provided with an insulating coating.

18. The feedthrough array of claim 1 further including an electronics module assembly and wherein the means for minimizing electromagnetic coupling includes a shield plate extending outwardly from the electronics module assembly between the filtered feedthrough and the unfiltered feedthrough.

19. The feedthrough array of claim 1 wherein the means for minimizing electromagnetic coupling includes a shielding manifold extending along at least a portion of the filtered feedthrough.

20. The feedthrough array of claim 19 wherein the shielding manifold includes a capacitive filter.

21. The feedthrough array of claim 19 wherein the shielding manifold includes an end surface adjacent the unfiltered feedthrough and the end surface is provided with an electrically conductive coating.

22. The feedthrough array of claim 19 further including an electronics module assembly and wherein the shielding manifold extends inwardly from the electronics module assembly.

23. The feedthrough array of claim 22 further including a second shielding manifold extending outwardly from the electronics module assembly.

24. The feedthrough array of claim 19 wherein the shielding manifold includes an inner wall forming a feedthrough pin lumen and wherein the inner wall includes a ferrite lining.

25. The feedthrough array of claim 1 further including at least one filtered feedthrough contact pad and wherein the means for minimizing electromagnetic coupling includes a substrate for the filtered contact pad formed from a dielectric material.

26. The feedthrough array of claim 25 wherein the filtered contact pad substrate includes an embedded capacitive filter.

27. The feedthrough array of claim 25 wherein the filtered contact pad substrate includes an end surface adjacent the unfiltered feedthrough and the end surface is provided with an electrically conductive coating.

28. The feedthrough array of claim 1 wherein the means for minimizing electromagnetic coupling comprises a material including ferrite.

29. The feedthrough array of claim 1 wherein the means for minimizing electromagnetic coupling includes means for minimizing radiation from the unfiltered feedthrough comprising one of a ferrite material and a shielded conductor electrically coupled to internal circuitry of an implantable medical device and incorporating the unfiltered feedthrough pin.

30. The feedthrough array of claim 1 further comprising a ground line providing a ground path to a medical device housing.

31. The feedthrough array of claim 14 wherein the means for minimizing electromagnetic coupling includes one of: a coaxial cable, a strip line conductor, and a microstrip line conductor.

32. The feedthrough array of claim 1 further comprising:
a capacitive filter array disposed within the ferrule;
the at least one filtered feedthrough extending through the capacitive filter array,
the at least one unfiltered feedthrough not extending through the capacitive filter array.

* * * * *

UNITED STATES PATENT AND TRADEMARK OFFICE
CERTIFICATE OF CORRECTION

| | | |
|---|---|---|
| PATENT NO. | : 8,160,707 B2 | |
| APPLICATION NO. | : 11/343106 | |
| DATED | : April 17, 2012 | |
| INVENTOR(S) | : Iyer et al. | |

It is certified that error appears in the above-identified patent and that said Letters Patent is hereby corrected as shown below:

Col. 15, line 66, delete "feedthrouqh" and insert in place thereof -- feedthrough --.

Signed and Sealed this
Twelfth Day of March, 2013

Teresa Stanek Rea
*Acting Director of the United States Patent and Trademark Office*